(12) United States Patent  (10) Patent No.: US 7,738,762 B2
Melville et al.  (45) Date of Patent: *Jun. 15, 2010

(54) ATTACHING OPTICAL FIBERS TO ACTUATOR TUBES WITH BEADS ACTING AS SPACERS AND ADHESIVES

(75) Inventors: Charles David Melville, Seattle, WA (US); Richard S. Johnston, Sammamish, WA (US)

(73) Assignee: University of Washington, Seattle, WA (US)

( * ) Notice: Subject to any disclaimer, the term of this patent is extended or adjusted under 35 U.S.C. 154(b) by 4 days.

This patent is subject to a terminal disclaimer.

(21) Appl. No.: 12/288,517

(22) Filed: Oct. 20, 2008

(65) Prior Publication Data

US 2009/0103882 A1 Apr. 23, 2009

Related U.S. Application Data

(63) Continuation-in-part of application No. 11/640,525, filed on Dec. 15, 2006, now Pat. No. 7,447,415.

(51) Int. Cl.
*G02B 6/00* (2006.01)
*G02B 6/06* (2006.01)
*G02B 6/30* (2006.01)
*G02B 6/26* (2006.01)
*G02B 6/42* (2006.01)

(52) U.S. Cl. ................... 385/137; 385/39; 385/49; 385/116; 385/117

(58) Field of Classification Search ........... 385/137
See application file for complete search history.

(56) References Cited

U.S. PATENT DOCUMENTS 3,470,320 A  9/1969  Pike et al.

(Continued)

FOREIGN PATENT DOCUMENTS

EP  1077360  2/2001

(Continued)

OTHER PUBLICATIONS

Aloisi et al., "Electronic Linearization of Piezoelectric Actuators and Noise Budget in Scanning Probe Microscopy", Review of Scientific Instruments, vol. 77, No. 7, Jul. 5, 2006, pp. 073701-1 through 073701-6.

(Continued)

*Primary Examiner*—Uyen-Chau N Le
*Assistant Examiner*—Kajli Prince
(74) *Attorney, Agent, or Firm*—Blakely, Sokoloff, Taylor & Zafman LLP

(57) ABSTRACT

A scanning fiber device of one aspect may include an actuator tube. An optical fiber may be inserted through the actuator tube. The optical fiber may have a free end portion outside of the actuator tube. A first bead may be around the optical fiber. At least part of the first bead may be within a distal portion of the actuator tube. An adhesive may be adhering the first bead to the distal portion of the actuator tube. A second bead may be around the optical fiber. At least part of the second bead may be within a proximal portion of the actuator tube. An adhesive may be adhering the second bead to the proximal portion of the actuator tube.

23 Claims, 9 Drawing Sheets

U.S. PATENT DOCUMENTS

| | | |
|---|---|---|
| 3,644,725 A | 2/1972 | Lochridge, Jr. |
| 4,206,495 A | 6/1980 | McCaslin |
| 4,234,788 A | 11/1980 | Palmer et al. |
| 4,264,208 A | 4/1981 | Haberl et al. |
| 4,710,619 A | 12/1987 | Haberl |
| 4,743,283 A | 5/1988 | Borsuk |
| 4,768,513 A | 9/1988 | Suzuki |
| 4,770,185 A | 9/1988 | Silverstein et al. |
| 4,782,228 A | 11/1988 | Westell |
| 4,821,117 A | 4/1989 | Sekiguchi |
| 4,831,370 A | 5/1989 | Smoot |
| 4,872,458 A | 10/1989 | Kanehira et al. |
| 4,948,219 A * | 8/1990 | Seino et al. .................... 385/95 |
| 4,963,018 A | 10/1990 | West |
| 5,081,350 A | 1/1992 | Iwasaki et al. |
| 5,172,685 A | 12/1992 | Nudelman |
| 5,178,130 A | 1/1993 | Kaiya |
| 5,185,835 A | 2/1993 | Vial et al. |
| 5,315,383 A | 5/1994 | Yabe et al. |
| 5,360,968 A | 11/1994 | Scott |
| 5,454,807 A | 10/1995 | Lennox et al. |
| 5,455,669 A | 10/1995 | Wetteborn |
| 5,459,570 A | 10/1995 | Swanson et al. |
| 5,557,444 A | 9/1996 | Melville et al. |
| 5,596,339 A | 1/1997 | Furness, III et al. |
| 5,627,922 A | 5/1997 | Koelman et al. |
| 5,664,043 A | 9/1997 | Donaldson et al. |
| 5,694,237 A | 12/1997 | Melville |
| 5,695,491 A | 12/1997 | Silverstein |
| 5,701,132 A | 12/1997 | Kollin et al. |
| 5,751,465 A | 5/1998 | Melville et al. |
| 5,784,098 A | 7/1998 | Shoji et al. |
| 5,822,073 A | 10/1998 | Yee et al. |
| 5,822,486 A | 10/1998 | Svetkoff et al. |
| 5,887,009 A | 3/1999 | Mandella et al. |
| 5,894,122 A | 4/1999 | Tomita |
| 5,903,397 A | 5/1999 | Melville et al. |
| 5,913,591 A | 6/1999 | Melville |
| 5,939,709 A | 8/1999 | Ghislain et al. |
| 5,969,871 A | 10/1999 | Tidwell et al. |
| 5,982,528 A | 11/1999 | Melville |
| 5,982,555 A | 11/1999 | Melville et al. |
| 5,991,048 A | 11/1999 | Karlson et al. |
| 5,995,264 A | 11/1999 | Melville |
| 6,046,720 A | 4/2000 | Melville et al. |
| 6,049,407 A | 4/2000 | Melville |
| 6,061,163 A | 5/2000 | Melville |
| 6,069,698 A | 5/2000 | Ozawa et al. |
| 6,069,725 A | 5/2000 | Melville |
| 6,097,353 A | 8/2000 | Melville et al. |
| 6,154,321 A | 11/2000 | Melville et al. |
| 6,157,352 A | 12/2000 | Kollin et al. |
| 6,166,841 A | 12/2000 | Melville |
| 6,191,761 B1 | 2/2001 | Melville et al. |
| 6,204,832 B1 | 3/2001 | Melville et al. |
| 6,220,711 B1 | 4/2001 | Melville et al. |
| 6,243,186 B1 | 6/2001 | Melville et al. |
| 6,257,727 B1 | 7/2001 | Melville |
| 6,263,234 B1 | 7/2001 | Engelhardt et al. |
| 6,281,862 B1 | 8/2001 | Tidwell et al. |
| 6,285,505 B1 | 9/2001 | Melville et al. |
| 6,288,816 B1 | 9/2001 | Melville et al. |
| 6,291,819 B1 | 9/2001 | Hartley |
| 6,294,775 B1 | 9/2001 | Seibel et al. |
| 6,317,548 B1 | 11/2001 | Rockwell et al. |
| 6,369,953 B2 | 4/2002 | Melville et al. |
| 6,388,641 B2 | 5/2002 | Tidwell et al. |
| 6,411,838 B1 | 6/2002 | Nordstrom et al. |
| 6,441,359 B1 | 8/2002 | Cozier et al. |
| 6,492,962 B2 | 12/2002 | Melville et al. |
| 6,535,183 B2 | 3/2003 | Melville et al. |
| 6,538,625 B2 | 3/2003 | Tidwell et al. |
| 6,560,028 B2 | 5/2003 | Melville et al. |
| 6,563,105 B2 | 5/2003 | Seibel et al. |
| 6,581,445 B1 | 6/2003 | Weiss |
| 6,627,903 B1 | 9/2003 | Hirayanagi |
| 6,700,552 B2 | 3/2004 | Kollin et al. |
| 6,734,835 B2 | 5/2004 | Tidwell et al. |
| 6,747,753 B1 | 6/2004 | Yamamoto |
| 6,845,190 B1 | 1/2005 | Smithwick et al. |
| 6,850,673 B2 | 2/2005 | Johnston, II et al. |
| 6,856,712 B2 | 2/2005 | Fauver et al. |
| 6,867,753 B2 | 3/2005 | Chinthammit et al. |
| 6,959,130 B2 | 10/2005 | Fauver et al. |
| 6,975,898 B2 | 12/2005 | Seibel |
| 6,977,631 B2 | 12/2005 | Melville et al. |
| 7,068,878 B2 | 6/2006 | Crossman-Bosworth et al. |
| 7,123,790 B2 | 10/2006 | Rosman et al. |
| 7,159,782 B2 | 1/2007 | Johnston et al. |
| 7,184,150 B2 | 2/2007 | Qualing et al. |
| 7,189,961 B2 | 3/2007 | Johnston et al. |
| 7,230,583 B2 | 6/2007 | Tidwell et al. |
| 7,252,236 B2 | 8/2007 | Johnston et al. |
| 7,277,819 B2 | 10/2007 | Marcus et al. |
| 2001/0051761 A1 | 12/2001 | Khadem |
| 2001/0055462 A1 | 12/2001 | Seibel |
| 2002/0062061 A1 | 5/2002 | Kaneko et al. |
| 2002/0064341 A1 | 5/2002 | Fauver et al. |
| 2002/0080359 A1 | 6/2002 | Denk et al. |
| 2002/0093467 A1 | 7/2002 | Tidwell et al. |
| 2002/0093563 A1 | 7/2002 | Cline et al. |
| 2002/0097498 A1 | 7/2002 | Melville et al. |
| 2002/0139920 A1 | 10/2002 | Seibel et al. |
| 2003/0004412 A1 | 1/2003 | Izatt et al. |
| 2003/0010825 A1 | 1/2003 | Schmidt et al. |
| 2003/0010826 A1 | 1/2003 | Dvorkis et al. |
| 2003/0016187 A1 | 1/2003 | Melville et al. |
| 2003/0048540 A1 | 3/2003 | Xie et al. |
| 2003/0142042 A1 | 7/2003 | Tidwell et al. |
| 2003/0169966 A1 | 9/2003 | Tokizaki |
| 2003/0202361 A1 | 10/2003 | Johnston et al. |
| 2004/0061072 A1 | 4/2004 | Gu et al. |
| 2004/0122328 A1 | 6/2004 | Wang et al. |
| 2004/0153030 A1 | 8/2004 | Novak et al. |
| 2004/0196213 A1 | 10/2004 | Tidwell et al. |
| 2004/0212851 A1 | 10/2004 | Osakabe |
| 2004/0254474 A1 * | 12/2004 | Seibel et al. ................ 600/473 |
| 2005/0020926 A1 | 1/2005 | Wiklof et al. |
| 2005/0025368 A1 | 2/2005 | Glukhovsky |
| 2005/0085708 A1 | 4/2005 | Fauver et al. |
| 2005/0085721 A1 | 4/2005 | Fauver et al. |
| 2005/0174610 A1 | 8/2005 | Fukawa |
| 2005/0182295 A1 | 8/2005 | Soper et al. |
| 2005/0238277 A1 | 10/2005 | Wang et al. |
| 2006/0072189 A1 | 4/2006 | DiMarzio |
| 2006/0072843 A1 | 4/2006 | Johnston |
| 2006/0072874 A1 | 4/2006 | Johnston |
| 2006/0077121 A1 | 4/2006 | Melville et al. |
| 2006/0138238 A1 | 6/2006 | Johnston et al. |
| 2006/0149134 A1 | 7/2006 | Soper et al. |
| 2006/0186325 A1 | 8/2006 | Johnston et al. |
| 2006/0195014 A1 | 8/2006 | Seibel et al. |
| 2006/0226231 A1 | 10/2006 | Johnston et al. |
| 2006/0287647 A1 | 12/2006 | Torchia et al. |
| 2007/0081168 A1 | 4/2007 | Johnston et al. |
| 2007/0091426 A1 | 4/2007 | Johnston et al. |
| 2007/0129601 A1 | 6/2007 | Johnston et al. |
| 2007/0135693 A1 | 6/2007 | Melman et al. |
| 2007/0156021 A1 | 7/2007 | Morse et al. |
| 2007/0273930 A1 | 11/2007 | Berier et al. |

FOREIGN PATENT DOCUMENTS

| | | |
|---|---|---|
| EP | 1360927 | 11/2003 |

| | | |
|---|---|---|
| EP | 1864606 | 12/2006 |
| GB | 2057709 | 4/1981 |
| GB | 2378259 | 2/2003 |
| JP | 08211313 | 8/1996 |
| WO | WO-9300551 | 1/1993 |
| WO | WO-0174266 | 10/2001 |
| WO | WO-02/64341 | 5/2002 |
| WO | WO-03019661 | 3/2003 |
| WO | WO-2004040267 | 5/2004 |
| WO | WO-2004068218 | 8/2004 |
| WO | WO-2005009513 | 2/2005 |
| WO | WO-2006004743 | 1/2006 |
| WO | WO-2006041452 | 4/2006 |
| WO | WO-2006041459 | 4/2006 |
| WO | WO-2006071216 | 7/2006 |
| WO | WO-2006096155 | 9/2006 |
| WO | WO-2006/106853 | 10/2006 |
| WO | WO-2006104489 | 10/2006 |
| WO | WO-2006124800 | 11/2006 |
| WO | WO-2007070831 | 6/2007 |
| WO | WO-2008/033168 | 3/2008 |

OTHER PUBLICATIONS

Smithwick et al., "An Error Space Controller for a Resonating Fiber Scanner: Simulation and Implementation", *Journal of Dynamic Systems, Measurement and Control*, Fairfield, N.J., U.S., vol. 28.No. 4, XP009095153,ISSN: 0022-0434 (Dec. 2006) pp. 899-913.

Barhoum, Erek S., et al., "Optical modeling of an ultrathin scanning fiber endoscope, a preliminary study of confocal versus non-confocal detection", *Optics Express*, vol. 13, No. 19, (Sep. 8, 2005), pp. 7548-7562.

Brown, Christopher, et al., "A Novel Design for a Scanning Fiberoptic Endoscope", *Human Interface Technology Laboratory, University of Washington*, Seattle, WA 98195, Presented at SPIE's Regional Meeting on Optoelectronics, Photonics, and Imaging, (Nov. 1-2, 1999), 1 page.

Brown, Christopher M., et al., "Mechanical Design and Analysis for a Scanning Fiber Endoscope", *Proceedings of 2001 ASME Int'l Mechanical Engineering Congress and Exposition*, BED-vol. 51, (Nov. 11-16, 2001), 165-166.

Brown, Christopher M., et al., "Optomechanical design and fabrication of resonant microscanners for a scanning fiber endoscope", *Optical Engineering*, vol. 45, XP002469237, (Apr. 2006), pp. 1-10.

Chen, Tailian, et al., "Experiment of Coalescence of Dual Bubbles on Micro Heaters", *Department of Mechanical Engineering, University of Florida*, Gainesville, FL 32611-6300. USA., Printed from the Internet Aug. 13, 2006, 1-10.

Fauver, Mark, et al., "Microfabrication of fiber optic scanners", (2002) In *Proceedings of Optical Scanning II, SPIE 4773*, pp. 102-110., 9 pages.

Johnston, Richard S., et al., "Scanning fiber endoscope prototype performance", *Optical Fibers and Sensors for Medical Applications II, Proc. SPIE*, vol. 4616, (Oct. 13, 2004), 173-179.

PCT Search Report, and Written Opinion, PCT/US2007/011481, (1-15 pgs.)

PCT Search Report, and Written Opinion, PCT/US2007/011479, (May 28, 2008), 1-15 pgs.

PCT Search Report, and Written Opinion, "PCT/US2007/021604", (Jun. 2, 2008), 1-13 pgs.

Seibel, Eric J., et al., "A full-color scanning fiber endoscope", *Optical Fibers and Sensors for Medical Diagnosis and Treatment Applications. Ed. I Gannot. Proc. SPIE* vol. 6083, (2006), 9-16.

Seibel, Eric J., et al., "Microfabricated optical fiber with microlens that produces large field-of-view, video rate, optical beam scanning for microendoscopy applications", *Optical Fibers and Sensors for Medical Applications III, Proceedings of SPIE* vol. 4957, (2003), 46-55.

Seibel, Eric J., et al., "Modeling optical fiber dynamics for increased efficiencies in scanning fiber applications", *Optical Fibers and Sensors for Medical Applications V, proceedings of SPIE* vol. 5691, (2005), 42-53.

Seibel, Eric J., et al., "P-37: Optical fiber scanning as a microdisplay source for a wearable low vision aid", *Society for Information Display SID 2002*, Boston, MA, (May 19-24, 2002), 1-4.

Seibel, Eric J., et al., "Prototype scanning fiber endoscope", *Optical Fibers and Sensors for Medical Applications II, Proc. of SPIE*, vol. 4616, (2002), 1-7.

Seibel, Eric J., et al., "Single fiber flexible endoscope: general design for small size, high resolution, and wide field of view", *Human Interface Technology Laboratory, College of Engineering, University of Washington*, Seattle, WA, Proceedings of the SPIE, Biomonitoring and Endoscopy Technologies 4158, (2001), 11 pages.

Seibel, Eric J., et al., "Ultrathin laser scanning bronchoscope and guidance system for the peripheral lung", *11th World Conference on Lung Cancer*, (2005), p. 178.

Seibel, Eric J., et al., "Unique Features of Optical Scanning, Single Fiber Endoscopy", *Lasers in Surgery and Medicine 30*, (2002), 177-183.

Seibel, Eric, et al., "Unique Features of Scanning Fiber Optical Endopscopy", *2000 Annual Fall Meeting Abstracts T4.57*, (2000), 1.

Smithwick, Quinn Y., et al., "54.3: Modeling and Control of the Resonant Fiber Scanner for Laser Scanning Display or Acquisition" *Department of Aeronautics and Astronautics, University of Washington*, Seattle, WA SID 03 Digest, (2003), 1455-1457.

Smithwick, Quinn Y., et al., "A Nonlinear State-Space Model of a Resonating Single Fiber Scanner for Tracking Control: Theory and Experiment", *Transactions of The ASME*, vol. 126, (Mar. 2004), 88-101.

Smithwick, Quinn Y., et al., "Control Aspects of the Single Fiber Scanning Endoscope", (*2001*) *SPIE Optical Fibers and Sensors for Medical Applications*, 4253, 176-188., 15 pages.

Smithwick, Quinn Y., et al., "Depth Enhancement using a Scanning Fiber Optical Endoscope", *Department of Aeronautics, Human Interface Technology Laboratory, University of Washington*, Seattle, Washington, Optical Biopsy IV, Proc. SPIE 4613, (2002), 12 pages.

Tuttle, Brandon W., et al., "Delivery of therapeutic laser light using a singlemode silica fiber for a scanning fiber endoscope system", *Optical Fibers and Sensors for Medical Diagnostics and Treatment Applications VI, Proc. of SPIE* vol. 6083,, (2006), 608307-1 to608307-12.

Wang, Wei-Chih, et al., "Development of an Optical Waveguide Cantilever Scanner", *Opto-Ireland 2002: Optics and Photonics Technologies and Applications, Proceedings of SPIE* vol. 4876 (2003), 72-83.

Wang, Wei-Chih, et al., "Micromachined optical waveguide cantilever as a resonant optical scanner", *Department of Mechanical Engineering, University of Washington*, Seattle, WA 98195, *Sensors and Actuators A 102*, (2002), 165-175.

* cited by examiner

US 7,738,762 B2

ATTACHING OPTICAL FIBERS TO ACTUATOR TUBES WITH BEADS ACTING AS SPACERS AND ADHESIVES

RELATED APPLICATIONS

The present application is a continuation-in-part application that claims priority from, and fully incorporates herein, U.S. patent application Ser. No. 11/640,525, entitled "ATTACHING OPTICAL FIBERS TO ACTUATOR TUBES WITH BEADS ACTING AS SPACERS AND ADHESIVES", filed on Dec. 15, 2006 now U.S. Pat. No. 7,447,415, by Charles David Melville and Richard S. Johnston.

BACKGROUND

1. Field

Embodiments of the invention relate to scanning fiber devices. In particular, embodiments of the invention relate to attaching optical fibers to actuator tubes in scanning fiber devices.

2. Background Information

Various different types of scanning fiber devices are known in the arts. Scanning fiber devices commonly include a single, cantilevered optical fiber that may be vibrated or scanned in one or two dimensions according to a scan pattern.

FIG. 1 is a cross-sectional side view of one example of a known scanning fiber device 100. The scanning fiber device includes a housing 102. A piezoelectric tube 104 is included in the housing and attached to the housing with an attachment collar 106. A portion of an optical fiber 108 is inserted through the piezoelectric tube. A free end portion 110 of the optical fiber is within the housing and attached to an end of the piezoelectric tube. The free end portion is flexible and may resonate at a frequency that depends in part upon its length. The piezoelectric tube has electrodes 112. Wires 114 are electrically coupled with the electrodes. The electrodes may be driven to move the free end portion of the optical fiber according to an expanding spiral or other scan pattern. Dashed lines are used to show that the free end portion of the optical fiber may move during operation.

The movement of the optical fiber according to the scan pattern may be used to construct an image. Constructing an image may include displaying an image on a target area and/or acquiring an image of a target area. In displaying or forming an image on the target area, the light emitted from the end of the optical fiber may be modulated during the scan pattern depending on the pixel position in order to form a desired image on the target area. In acquiring an image of the target area, the scanning fiber device may scan an illumination spot through an optional lens system and over the target area in the scan pattern. Backscattered light may be captured, for example by a photosensor, in time series.

BRIEF DESCRIPTION OF THE SEVERAL VIEWS OF THE DRAWINGS

The invention may best be understood by referring to the following description and accompanying drawings that are used to illustrate embodiments of the invention. In the drawings.

DETAILED DESCRIPTION

In the following description, numerous specific details are set forth. However, it is understood that embodiments of the invention may be practiced without these specific details. In other instances, well-known structures and techniques have not been shown in detail in order not to obscure the understanding of this description.

Figure 1:
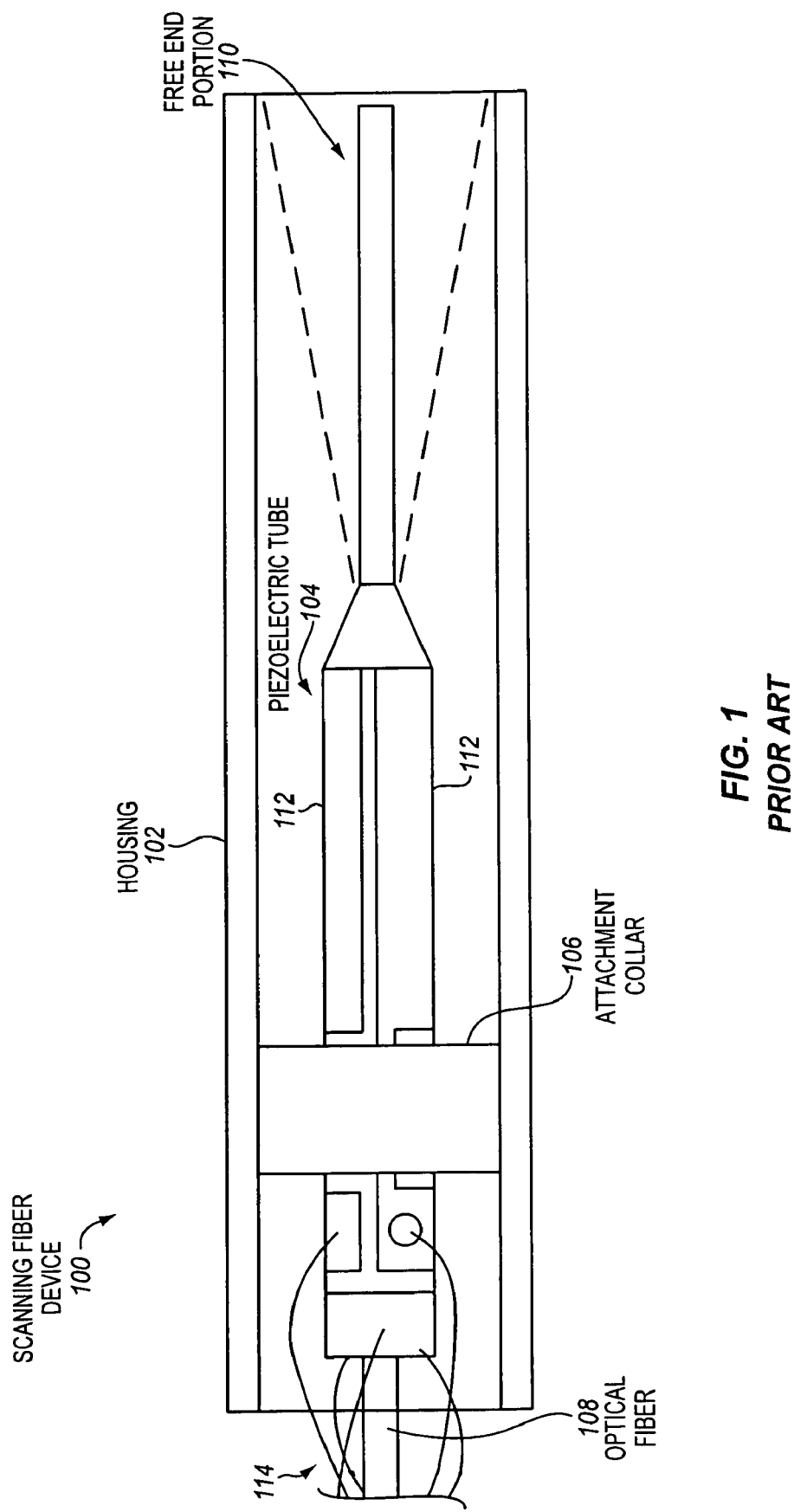
FIG. 1 is a cross-sectional side view of one example of a known scanning fiber device.
Figure 2:
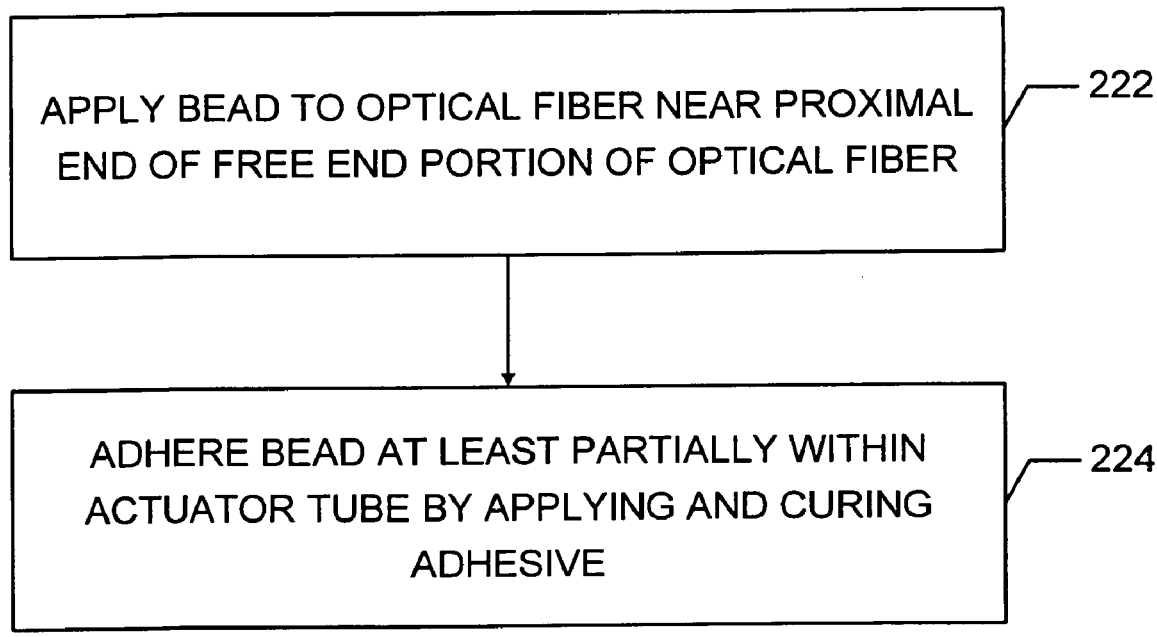
FIG. 2 is a block flow diagram of a method of attaching an optical fiber to an actuator tube during the manufacture of scanning fiber devices, according to embodiments of the invention.

FIG. 2 is a block flow diagram of a method of attaching an optical fiber to an actuator tube 220 during the manufacture of scanning fiber devices, according to embodiments of the invention. At block 222, a bead may be applied to an optical fiber of the scanning fiber device near a proximal end of a free end portion of the optical fiber. Then, the bead may be adhered at least partially within an actuator tube of the scanning fiber device by applying and curing an adhesive, at block 224.

The bead may serve as a spacer. If a single adhesive were to be applied to attach the optical fiber without the bead or spacer, the surface tension of the adhesive may tend to pull or draw the optical fiber away from the center of the tube towards the side of the tube from which the drop of adhesive was applied. This may tend to promote asymmetric movement of the optical fiber and may adversely affect the quality of the images constructed using the scanning fiber device. However, using the bead serving as a spacer may help to prevent or at least reduce movement of the optical fiber away from the center of the actuator tube due to the surface tension of the adhesive.

In one or more embodiments of the invention, a diameter or other cross-sectional dimension of the bead may be approximately equal to, or at least a substantial percentage of, an inner diameter or other cross-sectional dimension of the actuator tube, and the optical fiber may be substantially centered in the bead. Advantageously, this may help to accurately and consistently substantially center the optical fiber within the actuator tube at the point of attachment.

Figure 3:
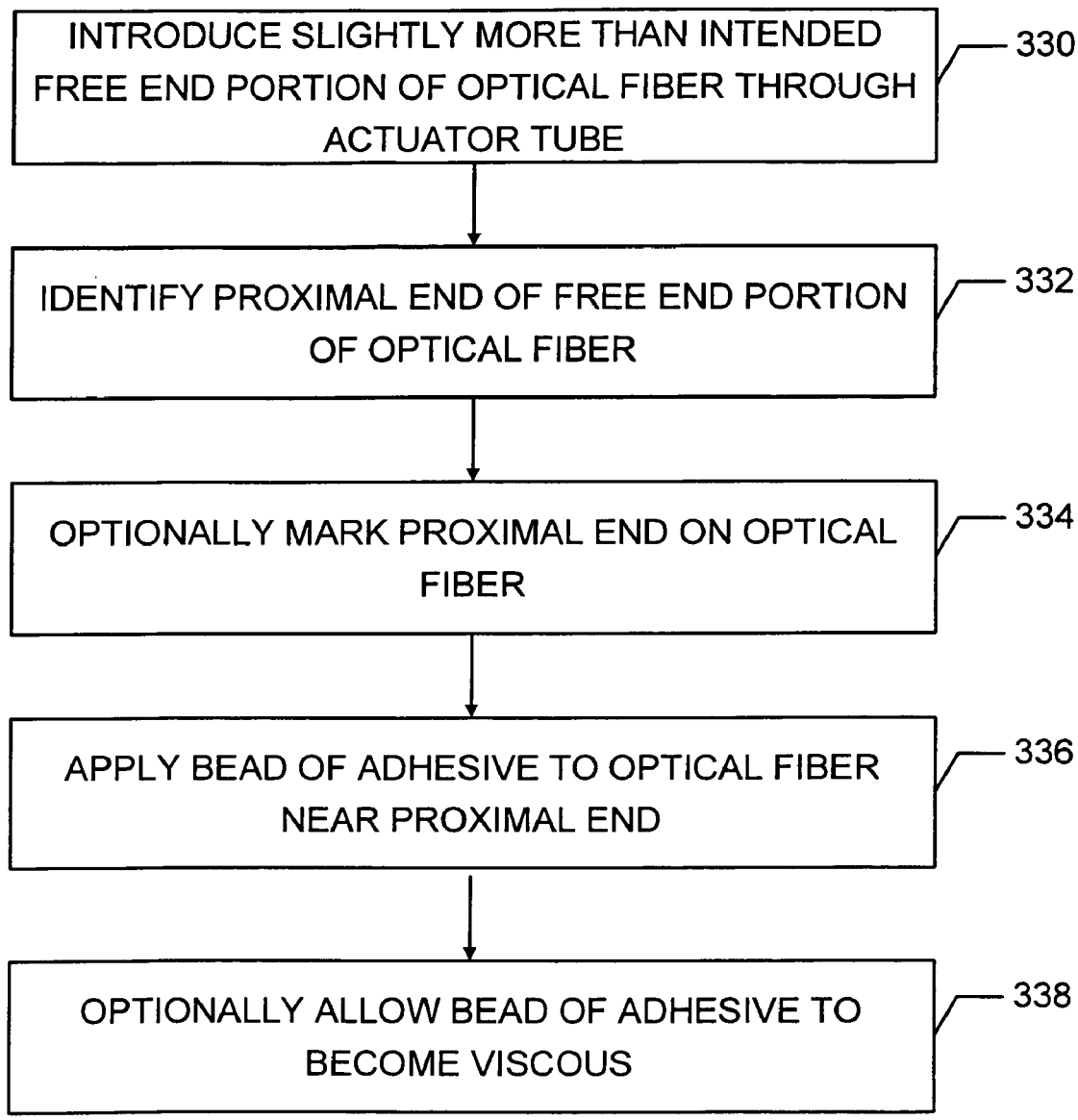
FIG. 3 is a block flow diagram of a method of applying a bead of adhesive near a proximal end of a free end portion of an optical fiber, according to one or more embodiments of the invention.

FIG. 3 is a block flow diagram of a method of applying a bead of adhesive near a proximal end of a free end portion of an optical fiber 322, according to one or more embodiments of the invention. The method may optionally be performed with the aid of a stereomicroscope or like device for viewing small objects.

At block 330, slightly more than an intended free end portion of an optical fiber of a scanning fiber device may optionally be inserted or otherwise introduced coaxially through an actuator tube. The free end portion may be located at the distal end of the optical fiber and may be the portion of the optical fiber that is flexible and scanned or otherwise moved in order to construct images. Slightly more than the intended free end portion of the optical fiber may be introduced through the actuator tube in order to provide additional room to apply the bead.

A proximal end of the free end portion of the optical fiber may be measured or otherwise identified, at block 332. The proximal end is one intended free end length measured back along the length of the optical fiber from the distal tip. In one aspect, a toolmakers microscope or like device may be used to make this measurement in order to promote accuracy. The word "end" in "proximal end" is not intended to imply that the optical fiber is necessarily cut or severed at this point.

Then, the proximal end may optionally be marked on the optical fiber, at block 334. For example, a small mark may be made on the optical fiber with a soft ink-based marker. Care should be taken to avoid scratching the optical fiber, as this may tend to promote breakage of the optical fiber during use. However, marking the proximal end is optional and not required.

At block 336, a bead of an adhesive may be applied to the optical fiber near the proximal end. The term "near the proximal end" may mean anywhere from about at the proximal end, to within about two inner diameters of the actuator tube to the proximal side of the proximal end. In one or more embodiments of the invention, the bead of the adhesive may be applied a slight distance, such as, for example, about one inner diameter of the actuator tube, to the proximal side of the proximal end. As will be explained further below, this slight distance between the bead and the proximal end may allow a cone of a subsequently applied adhesive to be formed from the bead tapering down towards the proximal end. Such a cone, which is not required, may help to distribute mechanical stresses, which may help to reduce breakage of the optical fiber.

The amount of adhesive that is applied may, in some cases, be quite small. One way of applying such a small bead of adhesive to an optical fiber, according to one or more embodiments of the invention, may include dipping an end of a small-diameter wire or other wirelike applicator in the adhesive, and then applying the second adhesive from the end of the wirelike applicator to the optical fiber. A smaller diameter tends to allow application of a relatively smaller amount of adhesive, while a larger diameter tends to allow application of a relatively larger amount of adhesive. In one aspect, the wirelike applicator may have a diameter that is on the order of that of the optical fiber, or less. For example, the diameter of the wirelike applicator may be around several hundred microns, or less. Alternatively, the bead of the adhesive may be applied to the optical fiber with a needle or like dispenser, or by other methods of applying small volumes of liquid known in the arts.

In one or more embodiments of the invention, applying the bead of the adhesive to the optical fiber may include substantially centering the optical fiber within the bead of the adhesive. If the adhesive is relatively viscous, this may include applying or wetting the adhesive around a circumference of the optical fiber, such as, for example, with the wirelike applicator. If the adhesive is less viscous, the adhesive may naturally tend to wet around the optical fiber, although applying the adhesive around the optical fiber may help. If desired, further centering of the optical fiber within the adhesive may optionally be achieved by spinning the optical fiber, applying sonic energy, otherwise agitating the applied adhesive, or the like.

Examples of suitable adhesives include, but are not limited to, various epoxies, cyanoacrylates, polyurethanes, and acrylics known in the arts. One specific example of a suitable adhesive is Copper-Bond brand epoxy resin, which is commercially available from Super Glue Corporation, of Rancho Cucamonga, Calif. Copper-Bond appears to be well suited for adhering to ceramic piezoelectric tubes, nickel ground electrodes, and glass optical fibers. The Copper-Bond additionally has a slight elasticity, which may help to dissipate mechanical stresses and/or provide dampening to help slow or stop the free end portion of the optical fiber between scan cycles. Another specific example of a suitable adhesive is TRA-BOND F123 brand adhesive, which is commercially available from TRA-CON, Inc., of Bedford, Mass. This adhesive tends to be somewhat more rigid than Copper-Bond. This rigidity may help to allow higher vibratory frequencies. Yet another suitable adhesive is 5 Minute® Epoxy brand epoxy resin, which is commercially available from Devcon, of Glenview, Ill. Another specific example of a suitable adhesive is SuperGlue brand cyanoacrylate, which is commercially available from Super Glue Corporation. Inorganic adhesives, such as, for example, frit glass, may also potentially be used. However, frit glass may tend to promote more frequent optical fiber breakage, potentially due at least in part to its rigidity.

Referring again to FIG. 3, the bead of the adhesive may optionally be allowed to become viscous, at block 338, before proceeding to adhere the bead of the adhesive to the actuator tube. In one aspect, allowing the bead of the adhesive to become viscous may include simply waiting for the adhesive to cure or otherwise harden to the desired extent.

In various embodiments of the invention, the viscosity may be increased by a factor of at least 2, 3, 4, 5, 10, 50, 100, 500, 1000, 5000, 10,000, or more. Completely curing the adhesive may cause the viscosity to increase by a relatively high factor. In one aspect, the viscosity may be increased to a point where the bead is capable of substantially maintaining its shape when contacted with the subsequently applied adhesive but capable of deforming slightly if forces greater than those of surface tension are applied. However, increasing the viscosity of the adhesive is optional and not required. For example, a sufficiently viscous starting adhesive may optionally be used to form the bead.

A particular method has been described, although the scope of the invention is not limited to this particular method. Many modifications to the method described above are possible and are contemplated. Certain operations may optionally be added to and/or removed from the method. For example, marking the proximal end and/or allowing the bead of adhesive to become viscous may optionally be omitted. As another example, actively centering the fiber in the bead by spinning or other approaches may optionally be added. As yet another example, introducing the free end portion of the optical fiber through the tube before applying the bead is optional. In another embodiment the bead may be applied before the free end portion is introduced through the tube. Certain operations may optionally be performed in different order. For example, identifying and marking the proximal end of the free end portion of the optical fiber may optionally be performed before introducing the free end portion of the optical fiber through the actuator tube. Other modifications are also contemplated. The method is therefore to be regarded as illustrative, rather than limiting.

Figure 4:
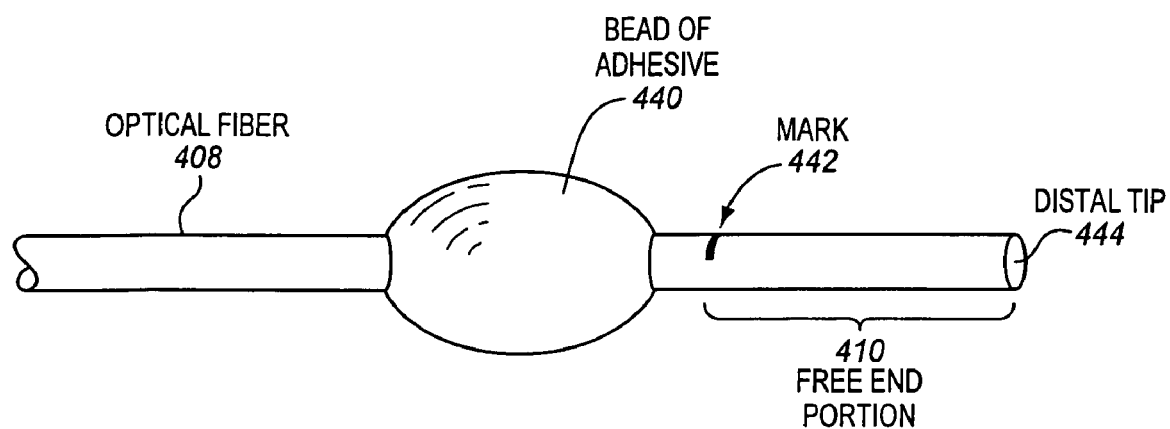
FIG. 4 is a perspective view of an example of a bead of adhesive applied to an optical fiber, according to one or more embodiments of the invention.

FIG. 4 is a perspective view of an example of a bead of adhesive 440 applied to an optical fiber 408, according to one or more embodiments of the invention. A mark 442 designates a proximal end of a free end portion 410 of the optical fiber measured from a distal tip 444. The particular illustrated bead of adhesive has a generally oval shape that is elongated along the axis of the optical fiber. Other shapes, such as spherical, sphereoidal, cylindrical, and other shapes, are also suitable. As shown, the optical fiber is substantially centered in the bead. In one or more embodiments of the invention, the bead of the adhesive may have a diameter that is at least 70%, or ranges from about 80 to 100%, of an inner diameter of an actuator tube in which the bead is to be at least partially introduced. If desired, the bead may optionally be introduced into the actuator tube to see if the size is appropriate and if appropriate the size of the bead may be adjusted by adding or removing adhesive.

Other methods of applying a bead to an optical fiber are also contemplated. For example, in one or more embodiments of the invention, applying a bead to the optical fiber may include inserting or introducing the optical fiber, such as, for example, a distal tip portion thereof, through a hole or opening of a pre-formed bead, and then sliding the pre-formed bead down a length of the optical fiber to near the proximal end of a free end portion. Once at the intended location, the pre-formed bead may be attached in place. One way of attaching the bead in place may include applying an adhesive. Alternatively, the pre-formed bead may include a hot-melt or thermoplastic material that may be melted to attach the bead to the optical fiber.

Figure 5:
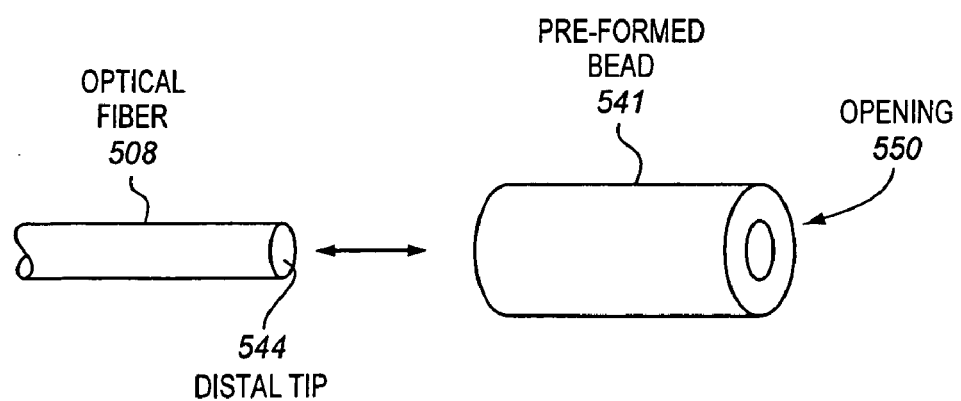
FIG. 5 is a perspective view of inserting an optical fiber through a hole or opening of a pre-formed bead, according to one or more embodiments of the invention.

FIG. 5 is a perspective view of inserting an optical fiber 508 through a hole or opening 550 of a pre-formed bead 541, according to one or more embodiments of the invention. The pre-formed bead is formed or shaped prior to being applied to the optical fiber. The particular illustrated pre-formed bead has a generally cylindrical shape, and has a generally cylindrically shaped coaxial hole with a diameter slightly larger than a diameter of the optical fiber. Other shapes, such as spherical, sphereoidal, oval, and other shapes, are also suitable. Examples of suitable materials for the pre-formed bead include, but are not limited to, adhesive materials, as well as ceramics, glasses, plastics, metals, and various other non-adhesive materials. Other characteristics of the pre-formed bead, such as, for example, its length and diameter, may be similar to, or the same as, those of the bead of adhesive.

Figure 6:
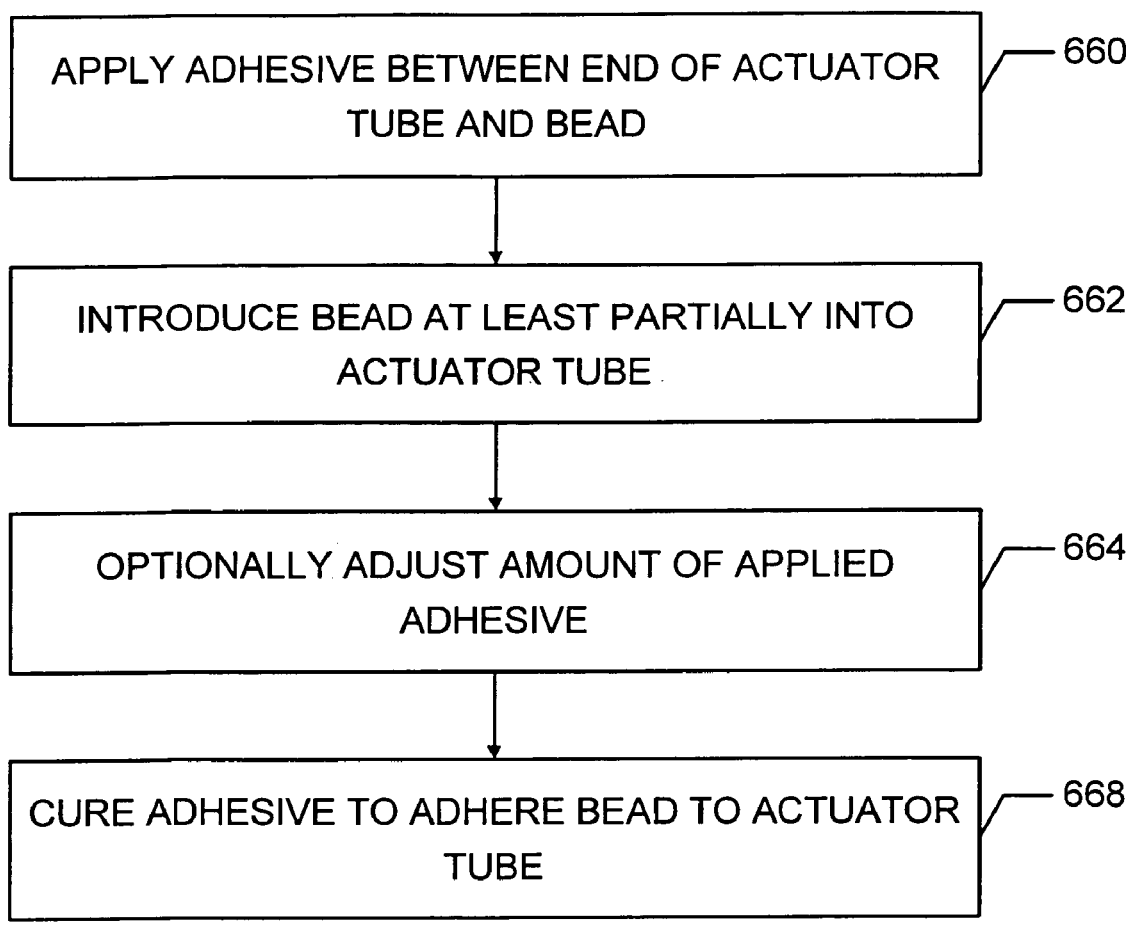
FIG. 6 is a block flow diagram of a method of adhering a bead at least partially within an actuator tube by applying and curing an adhesive, according to one or more embodiments of the invention.

FIG. 6 is a block flow diagram of a method of adhering a bead at least partially within an actuator tube by applying and curing an adhesive 624, according to one or more embodiments of the invention.

At block 660, an adhesive is applied between an end of the actuator tube and the bead. In various embodiments of the invention, the adhesive may be applied to one or more or all of an end of the actuator tube, the bead, and a portion of the optical fiber between the end of the actuator tube and the bead. In one aspect, an adhesive capable of wicking between the bead and the fiber, such as, for example, a low viscosity cyanoacrylate, may be applied at the bead/fiber interface to be introduced into the actuator tube. The adhesive may optionally be provided elsewhere, such as on the outer surface of the end of the tube.

Examples of suitable adhesives include, but are not limited to, the same types of adhesives mentioned before as being suitable for forming the bead of the adhesive. In particular, examples of suitable adhesives include, but are not limited to, epoxies, cyanoacrylates, polyurethanes, acrylics, and frit glass. If desired, a different adhesive may optionally be used in order to obtain one or more of a different viscosity, wicking rate, curing speed, curing temperature, cured hardness, cured glass transition temperature, color, index of refraction, or combinations thereof. In one or more embodiments of the invention, the adhesive used to form the bead may cure relatively quickly, such as at the rate of the 5-minute epoxy, and the adhesive used to adhere the bead may have a slightly longer curing or setting time to allow time to work, have relatively low amounts of wicking at time of application, and have good cured mechanical properties, although this is not required.

As before, the amount of adhesive that is applied may, in some cases, be quite small. As previously discussed, one way of applying such a small amount of adhesive, according to one or more embodiments of the invention, may include dipping an end of a small-diameter wire or other wirelike applicator in the adhesive, and then applying the second adhesive from the end of the wirelike applicator to the optical fiber. Alternatively, the adhesive may be applied with a needle or like dispenser, or by other methods of applying small volumes of liquid known in the arts.

Referring again to FIG. 6, the bead may be backed into or otherwise introduced at least partially or fully into the actuator tube, at block 662. As the bead is introduced into the actuator tube, at least some of the adhesive may be drawn and/or pushed into the actuator tube. The adhesive may also wet at least partially or fully around the bead. The surface tension may tend to be relaxed or reduced when the bead is just fully introduced into the actuator tube and substantially centered in the actuator tube surrounded by the adhesive. This aspect may help to promote accurately and consistently centering of the bead within the actuator tube.

At block 664, the amount of applied adhesive may optionally be adjusted. This may be performed while the bead is being introduced into the actuator tube, or after the bead has been introduced into the actuator tube, or at both times. Adjusting the amount of the applied adhesive may include removing some of the applied adhesive, adding additional adhesive, or both.

As previously mentioned, one possible way of adding additional adhesive may involve dipping an end of a small-diameter wire or other wirelike applicator in the adhesive, and then applying the adhesive from the end of the wirelike applicator. A similar approach may be used to remove some of the applied adhesive. A dry small-diameter wire or other wirelike device may be dipped in or otherwise contacted with the already applied adhesive and removed to remove some of the already applied adhesive. Alternatively, the adhesive may be removed with a small sorbent, capillary, needle, or by other approaches for removing small volumes of liquid known in the arts.

Multiple adjustments may optionally be made until a sufficient amount of the adhesive has been applied. In one aspect, the amount of adhesive is sufficient when the bead is fully introduced into the actuator tube and surrounded on all sides by adhesive capable of firmly adhering the bead to the actuator tube.

In one or more embodiments of the invention, the amount of adhesive may optionally be adjusted to form a cone of the adhesive at the end of the actuator tube. The cone may have an apex located near the proximal end of the free end portion of the optical fiber. In one or more embodiments, the cone may have an angle in the range of about 30 to 60°, such as, for example, approximately 45°. Such a cone may help to distribute mechanical stresses at the point of attachment of the optical fiber, which may help to reduce breakage of the optical fiber. However, the use of such a cone is optional, and not required.

Then, the adhesive may be cured to adhere the bead to the actuator tube, at block 668. For some adhesives, curing the adhesive may include simply waiting for a period of time that is sufficient for the adhesive to cure. For many adhesives, this period of time ranges from several minutes to several hours.

In the case of a certain ultraviolet radiation curable adhesives, such as, for example, certain acrylates, curing the adhesive may include transmitting ultraviolet or other suitable actinic radiation to the adhesive.

A particular method has been described, although the scope of the invention is not limited to this particular method. Certain operations may optionally be added to and/or removed from the method. For example, adjusting the amount of adhesive is optional and may be omitted. Certain operations may optionally be performed in different order. For example, adjustment may be performed before introducing, or after curing, or both. Other modifications are also contemplated. The method is therefore to be regarded as illustrative, rather than limiting.

To further illustrate certain concepts, consider the following detailed example of a method of adhering a bead at least partially within an actuator tube by applying and curing an adhesive, according to one particular embodiment of the invention. However, it is to be understood that this particular example is merely illustrative, and not limiting. Initially a small-diameter wire or other wirelike applicator may be dipped into an adhesive. Then the applicator having the adhesive thereon may be worked around a circumference of a portion of the optical fiber just to the proximal side of the bead between the bead and the end of the actuator tube. Then the applicator may again be dipped into the adhesive and the applicator having the adhesive thereon may be worked around the end of the actuator tube. Enough adhesive may be applied to wet with the previously applied adhesive and optionally start to form a cone down from the end of the actuator tube to the proximal side of the bead. Then the applicator may be dipped into the adhesive again and the applicator having the adhesive thereon may optionally be worked around an outside circumference of the actuator tube up to several hundred micrometers in from the end where the optical fiber is to be attached. If desired, the amount of adhesive applied may optionally be adjusted to form a cone sloping down from the end of the actuator tube to the proximal side of the bead. In one aspect, the cone may optionally have an angle of around 45°.

Figure 7A:
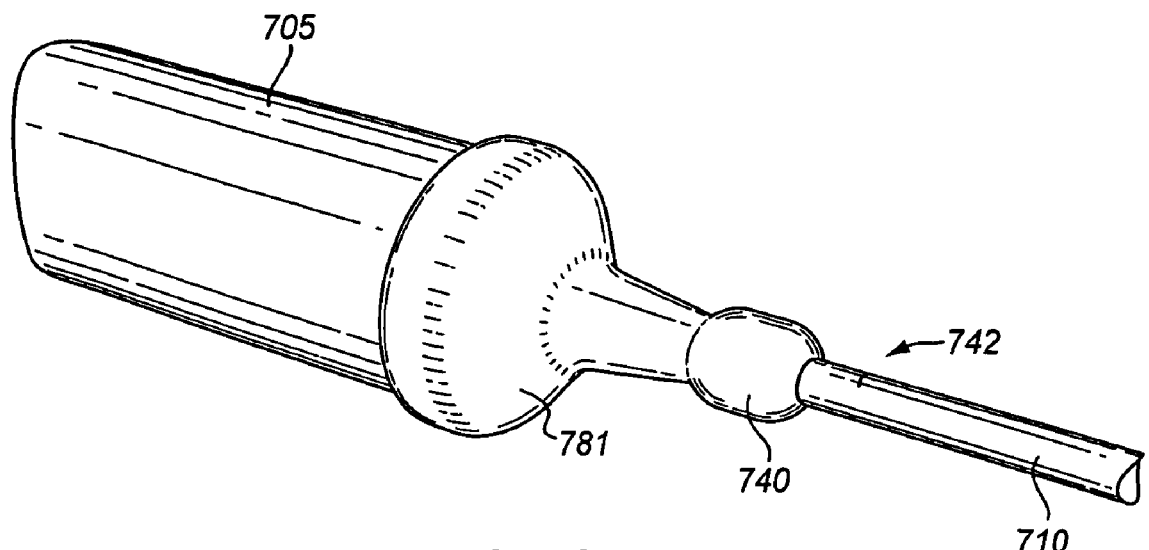
FIG. 7A is a perspective view illustrating a cone of adhesive applied between an end of an actuator tube and a bead, according to one or more embodiments of the invention.

FIG. 7A is a perspective view illustrating a cone of adhesive 781 applied between an end of an actuator tube 705 and a bead 740, according to one or more embodiments of the invention. In addition, adhesive has been applied to around a circumference at the end of the actuator tube. A mark 742 is used to designate the proximal end of the free end portion of the optical fiber 710.

After the cone of adhesive has been applied, the bead may then be backed into or otherwise introduced fully into the actuator tube. If the bead is slightly removed from the proximal end of the free end portion of the optical fiber, then the proximal end may be backed into or otherwise introduced slightly into the actuator tube so that the adhesive in the tube wets to the proximal end. As the bead is introduced into the actuator tube, at least some of the adhesive may be drawn and/or pushed into the actuator tube. This adhesive may wet the bead and the bead may be centered within the actuator tube surrounded by this adhesive. If desired, the bead may optionally be introduced and de-introduced several times to promote good wetting.

Figure 7B:
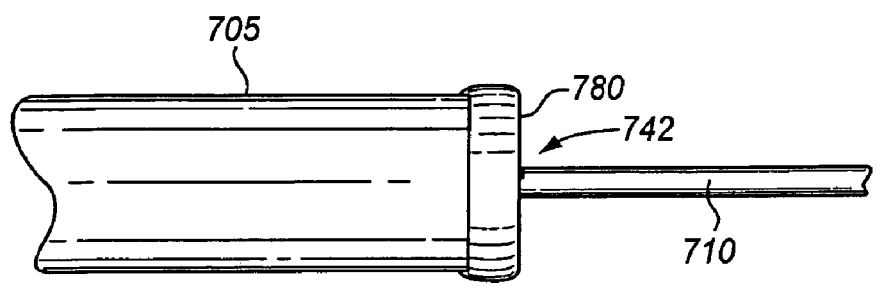
FIG. 7B is a perspective view illustrating introduction of the bead fully into the actuator tube until the mark designating the proximal end of the free end portion is in contact with and wetted by the adhesive in the tube, according to one or more embodiments of the invention.

FIG. 7B is a perspective view illustrating introduction of the bead 740 fully into the actuator tube 705 until the mark 742 designating the proximal end of the free end portion is in contact with and wetted by the adhesive in the tube, according to one or more embodiments of the invention. This is useful for forming a cone from the bead to the proximal end of the free end portion, as described further below.

Then the proximal end may be pulled out of, or otherwise removed from, the actuator tube, for example, by a distance of around one inner diameter of the actuator tube. At least part of the bead may remain in the actuator tube at the end of the actuator tube. Additional adhesive may be applied with the applicator, if appropriate, to form a cone from the end of the actuator tube down to the proximal end of the free end portion. In one aspect, the cone may have an angle of about 45°.

A particular example has been shown and described, although the scope of the invention is not limited to this particular example. Many alternate embodiments of the invention are also contemplated. For example, applying the adhesive between the end of the actuator tube and the bead may include applying the adhesive: (1) only around the end of the bead closest to the actuator tube; (2) only around the center of the bead; (3) only around an inside surface of the end of the actuator tube; (4) only to the optical fiber just to the proximal side of the bead; (5) at various combinations of these locations. As other examples, the adhesive may be applied without forming a cone down to the bead and/or a cone down to the proximal end of the free end portion of the optical fiber.

Figure 8:
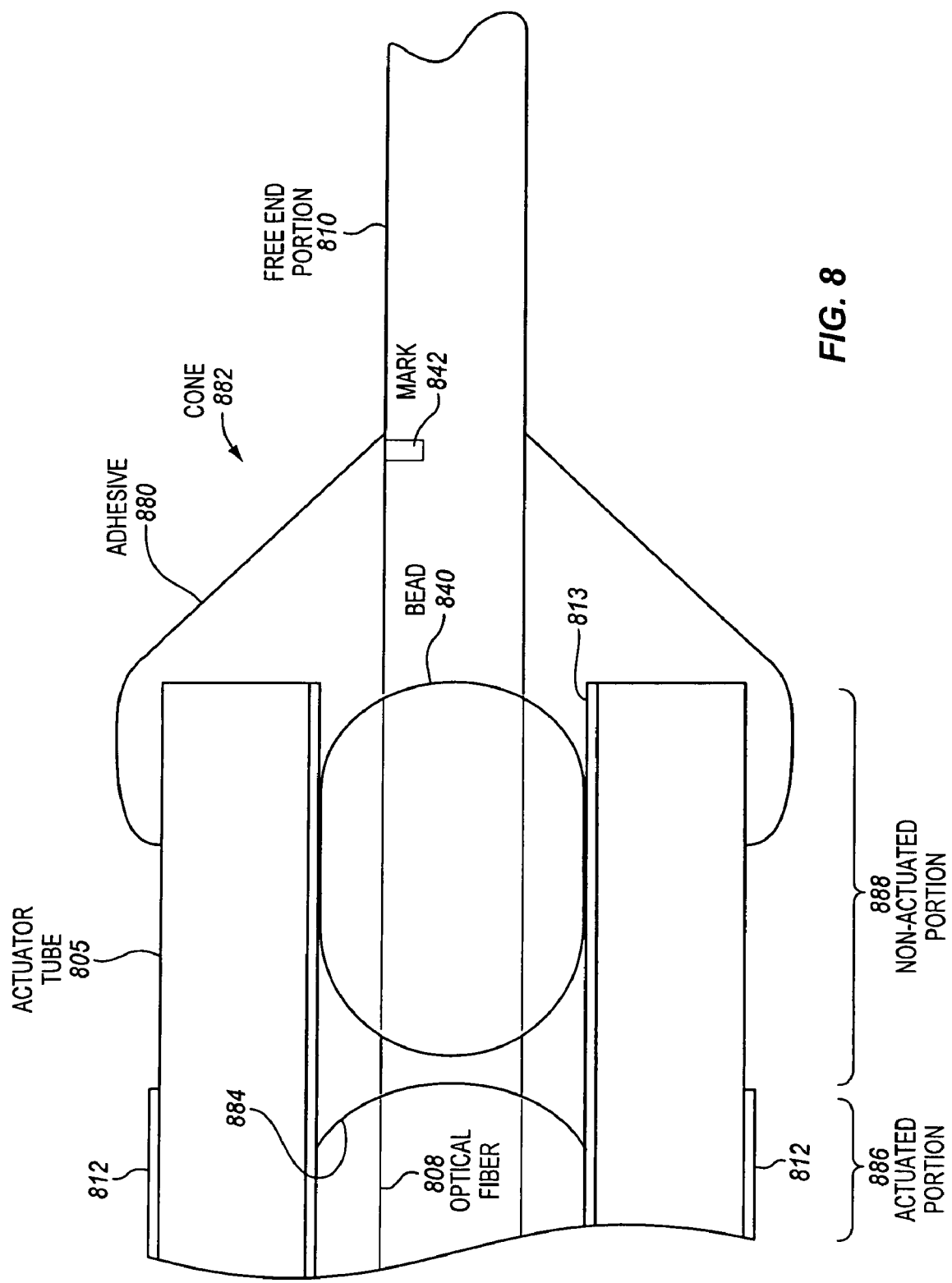
FIG. 8 is a cross-sectional side view of a portion of a scanning fiber device taken down the center of an actuator tube near a point of attachment of a free end portion of an optical fiber, according to one or more embodiments of the invention.

FIG. 8 is a cross-sectional side view of a portion of a scanning fiber device taken down the center of an actuator tube 805 near a point of attachment of a free end portion 810 of an optical fiber 808, according to one or more embodiments of the invention. The view conceptually shows one example of how the optical fiber and the actuator tube may be attached by a bead 840 and an adhesive 880.

The optical fiber is inserted through the actuator tube. Examples of suitable actuator tubes for various embodiments of the invention include, but are not limited to, piezoelectric tubes, electroactive polymer tubes, and other types of transducer tubes known in the arts. The tubes may be cylindrical. Alternatively, the tubes may have a transverse cross-section of an oval, square, rectangle, hexagon, octagon, or other regular polygonal shape.

The free end portion of the optical fiber lies outside of the actuator tube. In particular, the free end portion of the optical fiber lies to the distal end of the actuator tube, which is on the right-hand side of the illustration. In the illustration, an optional mark 842 identifies the proximal end of the free end portion of the optical fiber. The proximal end of the free end portion of the optical fiber is attached to the actuator tube. The bead is included around the optical fiber near the proximal end. In one or more embodiments of the invention, the center of the bead may be located within two inner diameters of the actuator tube, such as, for example, about one inner diameter, towards the actuator tube from the proximal end. However, the scope of the invention is not limited in this respect.

The cross section of the bead along an axis of the optical fiber has a substantially oval shape. The oval shape is elongated along the axis of the optical fiber. Alternatively, square, rectangular, circular, or other cross-sectional shapes may optionally be used. As shown, the optical fiber is substantially centered within the bead. As further shown, the bead and the optical fiber are each substantially centered in the actuator tube at the end of the tube. The bead may serve as a spacer to help promote that the adhesive does not pull the optical fiber to one side.

The adhesive adheres the bead to the actuator tube. The adhesive substantially surrounds the bead on all sides. The bead and the adhesive abut at an interface that may be more or less perceptible depending upon the particular materials used for the bead and the adhesive. In one or more embodiments of the invention, the bead and the adhesive may each comprise substantially the same material. In which case, the interface may be relatively less perceptible, but still typically perceptible by the presence of bubbles, imperfect adhesion, or other forms of imperfect material matching at the interface. In one or more other embodiments, the bead and the adhesive may comprise different materials. The different materials may potentially have different mechanical properties, such as, for example, hardness or elasticity, different optical properties, such as, for example, different color or transparency, and other different properties. In one or more embodiments, the bead may be more elastic than the adhesive in order to help provide some dampening to help stop the fiber from vibrating and/or distribute mechanical stresses to help reduce breakage.

As shown, in one or more embodiments of the invention, the adhesive may be formed into a cone 882 at the end of the actuator tube. The cone has an apex located near the proximal end. The cone has an angle to the apex that is in the range of about 30 to 60°, such as, for example, about 45°. The cone, which is not required, may help to distribute mechanical stresses at the point of attachment of the optical fiber, which may help to reduce breakage of the optical fiber. Depending upon the wetability and surface tension characteristics, the adhesive may form a meniscus 884 with the actuator tube.

As previously mentioned, one suitable type of actuator tube is a piezoelectric tube. Suitable piezoelectric tubes are commercially available from several sources including, but not limited to: Morgan Technical Ceramics Sales, of Fairfield, N.J.; Sensor Technology Ltd., of Collingwood, Ontario, Canada; and PI (Physik Instrumente) L.P., of Auburn, Mass.

The particular illustrated piezoelectric tube optionally includes an actuated portion 886, and a non-actuated portion 888. Metal electrodes 812 are included on an outside surface of the actuated portion of the piezoelectric tube. The metal electrodes on the outside surface may drive the actuator tube. Such metal electrodes are absent from the outside surface of the non-actuated portion. In one aspect, the non-actuated portion may have a length of around one inner diameter of the actuator tube, although this is not required. An optional ground metal electrode 813 is included on the inside surface of the piezoelectric tube in both the actuated and non-actuated surface. The adhesive adheres the bead to the non-actuated end. Including such a non-actuated end where the free end portion of the optical fiber is attached may help to reduce mechanical stresses that may over time otherwise tend to damage either the optical fiber or piezoelectric tube and/or change the firmness of the attachment. However, such inclusion of the non-actuated end is optional and not required.

To further illustrate certain concepts, consider a detailed working example of a scanning fiber device according to one or more embodiments of the invention. It is understood that this example is to be construed as merely illustrative, rather than limiting.

Figure 9:
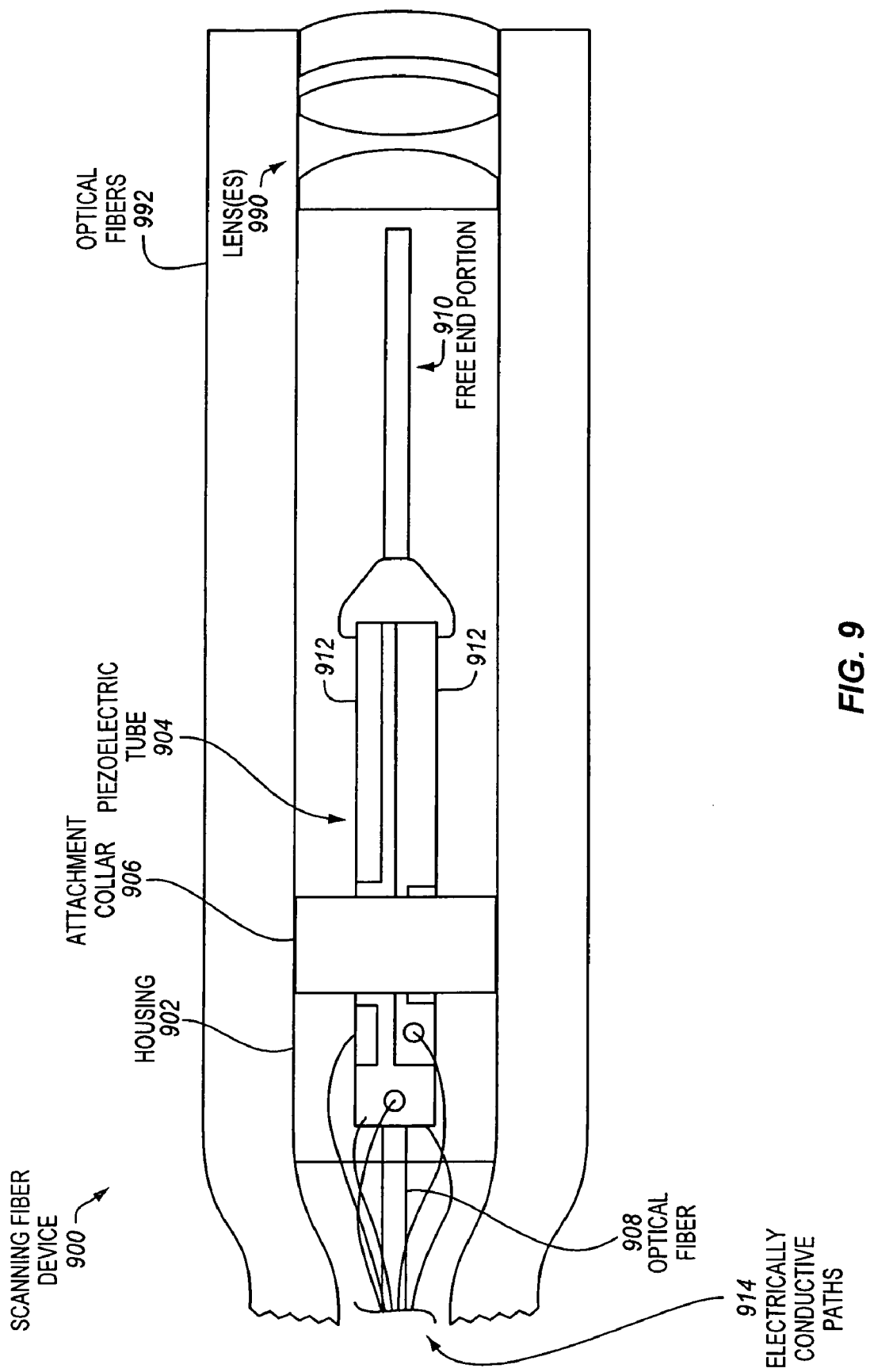
FIG. 9 is a cross-sectional side view of a detailed example of a scanning fiber image capture device, according to one or more embodiments of the invention.

FIG. 9 is a cross-sectional side view of a detailed example of a scanning fiber image capture device 900, according to one or more embodiments of the invention. The particular illustrated scanning fiber device is well suited for use as an endoscope or other instrument or probe to be inserted into patients.

The scanning fiber device includes a housing 902. The housing may include stainless steel or other materials suitable for deployment in patients. The housing may be sufficiently hermetically sealed for insertion into a patient as an endoscope or like instrument or probe. The housing may be small or minute. For example, in one or more embodiments of the invention, the housing may be generally tubular, have a diameter or other cross-sectional dimension that is on the order of about 5 millimeters (mm) or less, and have a length that is on the order of about 20 mm, or less. Such a minute housing may offer certain advantages when the scanning fiber device is to be used as an endoscope or otherwise inserted into a patient, although in other implementations the size and shape of the housing may vary considerably.

A free end portion 910 of an optical fiber 908 is included within the housing. A piezoelectric tube 904 is also included within the housing. The piezoelectric tube represents one possible type of actuator tube. In one or more embodiments of the invention, the piezoelectric tube may include a PZT 5A material, although this is not required. In one aspect, the piezoelectric tube having the attached free end portion of the optical fiber may be introduced into the housing during manufacture of the scanning fiber device.

The optical fiber is inserted through a generally cylindrical opening in the piezoelectric tube. The optical fiber may be attached to the distal end of the piezoelectric tube as disclosed elsewhere herein. The optical fiber may also optionally be attached to the proximal end of the piezoelectric tube. The optical fiber need not be attached with the use of a bead as a spacer on this proximal end of the piezoelectric tube, although it may be if desired. An attachment collar 906 may couple the piezoelectric tube with the housing. The piezoelectric tube may be inserted through a tightly fitting generally cylindrical opening through the attachment collar.

A number of wires or other electrically conductive paths 914 are run from an endoscope base station (not shown) to the proximal end of the scanning fiber device. The electrically conductive paths may carry electrical signals to the piezoelectric tube. In one or more embodiments, the piezoelectric tube may have four, quadrant metal electrodes 912 on an outer surface thereof to move the optical fiber in two dimensions. Each of four electrically conductive paths may be soldered to or otherwise electrically coupled with respective ones of four, quadrant electrodes on the piezoelectric tube. These four paths may carry drive signals to the piezoelectric tube to cause it to scan the optical fiber, for example in an expanding spiral scan pattern. In one or more embodiments, the piezoelectric tube may optionally have a ground electrode on an inside surface thereof. One conductive path may optionally be provided to the ground electrode. However, the scope of the invention is not limited to this particular type of piezoelectric tube or the connections thereto.

The device includes one or more lenses 990. The one or more lenses are positioned in an optical path of light directed through the free end portion of the optical fiber. In one or more embodiments of the invention, the one or more lenses may include lenses from Pentax Corporation, although this is not required.

In one or more embodiments of the invention, optical fibers 992 may be included around the outside of the housing to collect backscattered light from a target surface. By way of example, in the particular case of a full-color scanning fiber endoscope, twelve optical fibers may be included around the outside of the housing for collection of light. The optical fibers may collect and convey light back to photodetectors located at a proximal end of the scanning fiber device. However, the scope of the invention is not so limited.

As previously discussed in U.S. patent application Ser. No. 11/640,525, of which the present patent application is a continuation-in-part, in one or more embodiments, the bead and the adhesive may comprise different materials. The different materials may potentially have different mechanical properties, such as, for example, hardness or elasticity, different optical properties, such as, for example, different color or transparency, and other different properties. In one or more embodiments, the bead may be more elastic than the adhesive in order to help provide some dampening to help stop the fiber from vibrating and/or distribute mechanical stresses to help reduce breakage.

Accordingly, as previously discussed, a scanning fiber device, according to one or more embodiments of the invention, may include an actuator tube, and an optical fiber inserted through the actuator tube. The optical fiber may have a free end portion outside of the actuator tube. The device may also include a bead around the optical fiber, the bead at least partially within the actuator tube. An adhesive may be used to adhere the bead to the actuator tube. The bead and the adhesive may include different materials. The bead may be more elastic than the adhesive.

In one or more embodiments of the invention, at least a part, or all, of a bead that is to be introduced into an actuator tube may have a diameter that is greater than an inner diameter of the actuator tube. Introducing at least a part, or all, of the bead into the actuator tube may include compressing or otherwise restraining this greater diameter to be within the lesser inner diameter of the actuator tube. In one or more embodiments of the invention, at least a part, or all, of the bead that is to be introduced into the actuator tube may include a pliable material that is capable of being compressed, deformed, or otherwise restrained to be within the inner diameter of the actuator tube. The bead may be formed with a wire, wire-like applicator, or needle, as previously described.

Typically, the diameter of the part, or all, of the bead that is to be introduced into an actuator tube may be from about 1% to 60%, commonly from about 2% to 50%, often from 3% to 40%, and in some cases from about 4% to 30% greater than an inner diameter of the actuator tube. By this inner diameter is meant the inner diameter of the actuator tube at the location where the bead is to be introduced. These sizes are merely illustrative. Relatively larger beads may also optionally be used as long as the bead is sufficiently pliable, shrinkable, compactable, or otherwise capable of being introduced into the actuator tube.

In one or more embodiments of the invention, the pliable material may be or include a rubbery material. In one or more embodiments, the rubber material may be or include a polymer that includes silicon, such as, for example, a silicone rubber or silicone material. One particular example of a commercially available silicone material that is suitable is SIL-BIONE® LSR 4305 DEV brand heat curing silicone elastomer, which is commercially available from Rhodia Silicones North America. Rhodia has headquarters in Cranbury, N.J. This silicone material has a hardness of about 5 Shore A. In one or more embodiments of the invention, the pliable material may have a hardness ranging from about 2 to 90 Shore A, often from about 3 to 80 Shore A, sometimes less than 40 Shore A, whereas the adhesive used to adhere the pliable material may have a hardness greater than 95 Shore A, often greater than 98 Shore A. Other suitable pliable materials include, but are not limited to, room temperature vulcanization (RTV) silicone rubbers, which use chemicals instead of heat to cure. Still other suitable pliable materials include, but are not limited to, other types of rubbers and elastomers known in the art. It is not required that the materials include or be based on silicon.

The compressed or otherwise restrained bead within the actuator tube may seat flushly against the inner diameter of the actuator tube. The diameter of the bead within the actuator tube may be 100% of an inner diameter of the actuator tube at least along a circumference of the actuator tube. This may help to create or form a seal between part or all of the bead within the actuator tube and the inner diameter of the actuator tube. As discussed above, an adhesive may be used to adhere the bead to the actuator tube. Suitable adhesives include, but are not limited to, those disclosed above (e.g., epoxies, cyanoacrylates, etc.).

In one or more embodiments of the invention, at least part, or all, of the bead may be introduced into the actuator tube, and the aforementioned seal may be formed, before the adhesive is applied. The adhesive may be applied to the distal side of the bead or seal without being applied to the proximal side of the bead or seal. After applying the adhesive, the bead may be drawn in a proximal direction to an intended location, and the bead may serve as a plunger or sucker that may tend to suck or draw at least some of the adhesive into the actuator tube. This may help to reduce voids in the adhesive, which may promote good attachment strength.

The seal formed between the bead and the inner surface of the actuator tube may be operable to prevent, or at least restrict, the adhesive that is applied from the distal side of the bead from crossing from the distal side of the bead to the proximal side of the bead. Advantageously, this may help to reduce coating of the inner surface of the actuator tube just proximally of the bead with the adhesive. Such coating may otherwise tend to alter the characteristics of the actuator tube. For example, in the case of a piezoelectric tube, a coating with the adhesive may tend to make the piezoelectric tube more rigid or stiff, which may tend to increase dampening. The increased dampening may tend to increase the amount of energy needed to actuate the free end portion of the optical fiber. Accordingly, as a result of the seal, no adhesive, or at least less adhesive, may be present on the inside surface of the actuator tube just proximal to the bead.

In some cases, such as for elastic materials, the bead that is adhered to the actuator tube may be adhered in a state in which it is being stretched in a proximal direction. For example, polymeric chains of the elastic material may be stretched or elongated in the proximal direction.

As previously discussed in U.S. patent application Ser. No. 11/640,525, the optical fiber may be attached to the distal end of the piezoelectric tube. The optical fiber may also optionally be attached to the proximal end of the piezoelectric tube. The optical fiber need not be attached with the use of a bead as a spacer on this proximal end of the piezoelectric tube, although it may be if desired.

Accordingly, as previously discussed, a scanning fiber device, according to one or more embodiments of the invention, may include an actuator tube, and an optical fiber inserted through the actuator tube. The optical fiber may have a free end portion outside of the actuator tube. The device may also include a first bead around the optical fiber. The first bead may be at least partially within a distal end or portion of the actuator tube. An adhesive may be used to adhere the first bead to the distal end of the actuator tube. The device may also include a second bead around the optical fiber. The optical fiber may be attached with a proximal portion of the actuator tube with the second bead.

One potential advantage of attaching the optical fiber with the proximal portion of the actuator tube with the second bead is increased attachment strength and/or reliability. If only a single bead at the distal end of the actuator tube is used, then over time and/or with use the attachment of the optical fiber with the actuator tube may in some cases tend to fail or at least weaken. Forces axially aligned with the optical fiber, such as, for example, forces that pull and/or push on the optical fiber, which may be encountered during use, may tend to cause the attachment to fail or at least weaken. However, attaching the optical fiber with the proximal portion of the actuator tube with the second bead may tend to increase the attachment strength and/or reliability.

Another potential advantage of attaching the optical fiber with the proximal portion of the actuator tube with the second bead is improved centering of the optical fiber within the proximal portion of the actuator tube. This may help to prevent the optical fiber from contacting the proximal end of the actuator tube, which may potentially mechanically damage the optical fiber.

In one or more embodiments, the second bead may be adhered to the actuator tube with an adhesive at a position where the actuator tube is coupled with a housing that encloses the actuator tube. For example, with quick reference to FIG. 9, the second bead may be adhered to the piezoelectric tube 904 at the attachment collar 906.

In one or more embodiments, adhesive may optionally be applied or included within the actuator tube from just proximal to the second bead at least about halfway toward or all the way to the proximal end of the actuator tube. For example, with quick reference to FIG. 9, the second bead may be adhered to the piezoelectric tube 904 at the attachment collar 906 and adhesive may be included in the piezoelectric tube 904 from just proximal of the second bead at the attachment collar to the proximal end of the piezoelectric tube 904. Advantageously, this may further help to increase the attachment strength and/or reliability and may help to prevent or at least reduce forces axially aligned with the optical fiber from reaching the bead at the distal portion of the actuator tube.

In one or more embodiments of the invention, different adhesives may optionally be used to secure the first and second beads, although this is not required. For example, a relatively harder or more rigid adhesive may be used to attach the proximal bead, and a relatively less hard or less rigid adhesive may be used to attach the distal bead. Using a relatively harder or more rigid material to attach the proximal bead may provide a very strong attachment capable of resisting axial forces on the optical fiber. Using a relatively less hard or less rigid material to attach the distal bead may provide a good combination of strength, along with some softness to provide dampening. The dampening may help to stop the optical fiber from vibrating at the end of a cycle.

In one or more embodiments of the invention, a segment of the optical fiber between the first and second beads within the actuator tube may be free of adhesive. For example, with quick reference to FIG. 9, the first bead may be adhered near the distal end of the piezoelectric tube 904, the second bead may be adhered to the piezoelectric tube 904 at the attachment collar 906, and there may be no significant amount of adhesive within the actuator tube between the first and second beads. Adhesive on the cantilever portion of the actuator tube may tend to make the actuator tube rigid, which tends to promote dampening.

In one or more embodiments of the invention, at least a part, or all, of the second bead that is to be introduced into and adhered to the proximal portion of the actuator tube may have a diameter that is greater than an inner diameter of the proximal portion of the actuator tube. Introducing at least a part, or all, of the second bead into the actuator tube may include compressing or otherwise restraining this greater diameter of the second bead to be within the lesser inner diameter of the proximal portion of the actuator tube. In one or more embodiments of the invention, at least a part, or all, of the second bead that is to be introduced into and adhered to the proximal portion of the actuator tube may include a pliable material that is capable of being compressed, deformed, or otherwise restrained to be within the inner diameter of the proximal portion of the actuator tube. The same diameters and materials as mentioned above for the first bead are also suitable for the second bead. In one particular embodiment, both the first bead and the second bead have diameters greater than the inner diameter of the actuator tube and both comprise an elastic, rubber, or other pliable material.

Figure 10:
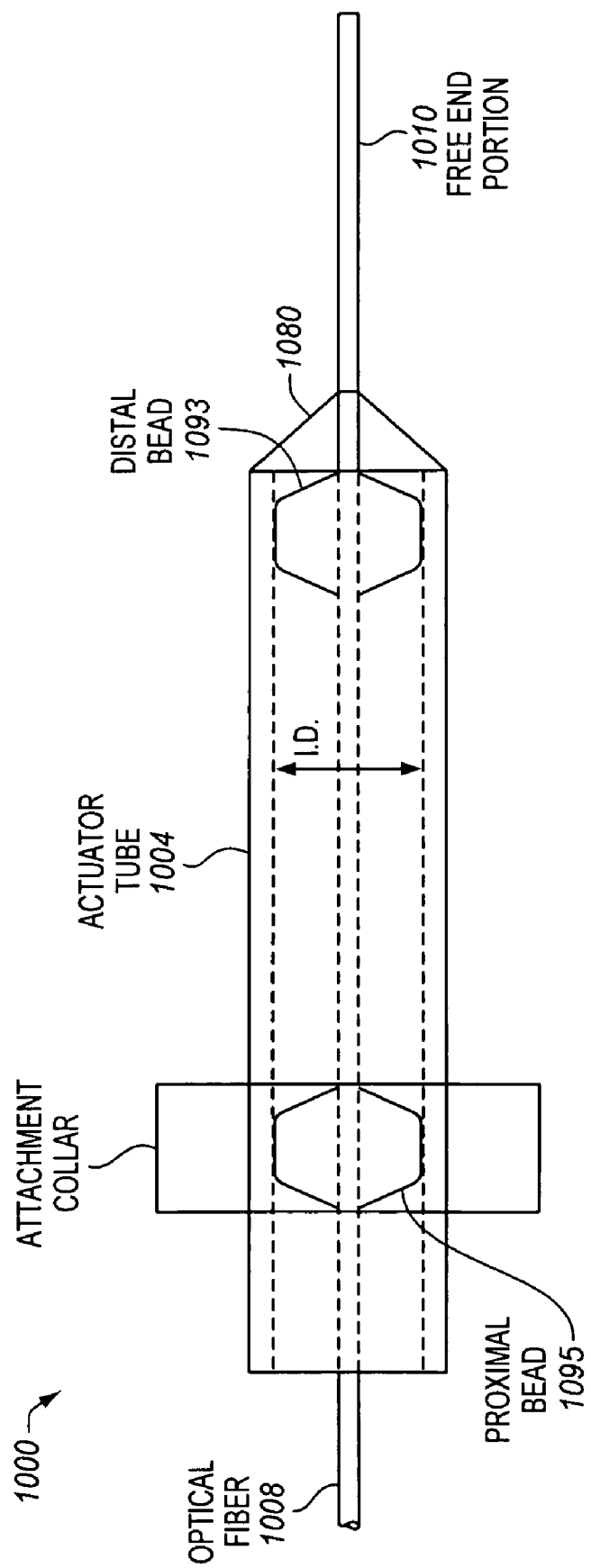
FIG. 10 is a cross-sectional side view of an example of a scanning fiber image capture device having two beads to attach an optical fiber to an actuator tube, according to one or more embodiments of the invention.

FIG. 10 is a cross-sectional side view of an example of a scanning fiber image capture device 1000 having two beads to attach an optical fiber to an actuator tube, according to one or more embodiments of the invention. The device includes an optical fiber 1008 having a free end portion 1010, an actuator tube 1004, an attachment collar 1006, a distal bead 1093, a proximal bead 1095, and an optional adhesive cone 1080. The distal bead is inside the actuator tube just inside from the distal end thereof. The proximal bead is inside the actuator tube at the attachment collar. In one or more embodiments, both of the beads may include a pliable material, and both of the beads, before insertion into the actuator tube, may be larger than an inner diameter of the actuator tube.

In order to illustrate certain concepts, consider the following detailed example of attaching an optical fiber to a piezoelectric tube using two pliable, elastic silicone beads. This example is understood to be merely illustrative, rather than limiting on the scope of the invention.

Start with a piezoelectric tube having an attachment collar mounted thereon. Also, start with an optical fiber having its jacket removed from the distal end a length slightly greater than an intended length of the flexible free end portion of the optical fiber plus the length of the piezoelectric tube.

Utilize a toolmakers microscope, stereomicroscope, or like device for viewing small objects to perform the following procedures. Insert the distal end of the optical fiber through the piezoelectric tube until a segment of the optical fiber having the intended locations of both beads extends distally from the distal end of the piezoelectric tube.

Identify the intended locations of the two beads. By way of example, a first bead may be just proximal of the distal end of the flexible free end portion of the optical fiber as previously described. A second bead may be intended to reside at the attachment collar when the first bead is at its intended location just proximal of the distal end.

Use a wire applicator, as previously described, to form both beads on the optical fiber using uncured SILBIONE® LSR 4305 DEV brand heat curing silicone elastomer. While forming the beads, measure the diameter of the beads, for example using the stereomicroscope or toolmakers microscope. Add and/or remove material from the bead until the beads are of the intended size. By way of example, if the inner diameter of the piezoelectric but is about 200 microns, the beads may have diameters of about 205-210 microns, although this size is not required.

Once the beads are of the intended sizes, heat cure the beads, such as, for example, using a temperature of about 130° C. for about 15 seconds. By way of example, a hot air tool similar to that used for surface mount devices may optionally be used. After the beads are cured, pull proximally on the optical fiber to draw the proximal bead until it is right at the proximal edge of the piezoelectric tube. Apply an adhesive to the proximal bead at the proximal edge of the piezoelectric tube. One non-limiting example of a suitable adhesive is TRA-BOND F123 brand adhesive, which is commercially available from TRA-CON, Inc., of Bedford, Mass. This adhesive provides a very strong attachment capable of resisting axial forces on the optical fiber. This adhesive also tends to remain strong over a relatively wide temperature range. However, use of this adhesive is not required.

Push on the optical fiber to make the proximal bead go back into the piezoelectric tube. The proximal bead will suck or draw some of the adhesive into the piezoelectric tube with it. This may help to reduce air voids in the adhesive, which may further increase the strength of the attachment. As previously discussed, the proximal bead may provide a seal with the piezoelectric tube to prevent the adhesive from wicking across the bead distally into the rest of the piezoelectric tube.

Continue pushing on the optical fiber until the distal bead just appears at the distal end of the piezoelectric tube. Apply an adhesive to the distal bead at the distal end of the piezoelectric tube. One non-limiting example of a suitable adhesive is 5 Minute® Epoxy brand epoxy resin, which is commercially available from Devcon, of Glenview, Ill. This adhesive provides a good combination of strength, along with some softness to provide dampening. The dampening may help to stop the optical fiber from vibrating at the end of a cycle. However, this particular adhesive is not required.

Pull proximally on the optical fiber until the distal bead is at the intended position just inside the piezoelectric tube with a cone of the adhesive leading down to the intended edge of the flexible free end portion of the optical fiber. The distal bead will suck or draw some of the adhesive into the piezoelectric tube with it. This may help to reduce air voids in the adhesive. As previously discussed, the distal bead may provide a seal with the piezoelectric tube to prevent the adhesive from wicking across the bead proximally into the rest of the piezoelectric tube.

Heat cure the adhesives. By way of example, they may be cured using a temperature of about 130° C. for several minutes. By way of example, a hot air tool similar to that used for surface mount devices may optionally be used.

In the description above, for the purposes of explanation, numerous specific details have been set forth in order to provide a thorough understanding of the embodiments of the invention. The particular embodiments described are not provided to limit the invention but to illustrate it. Embodiments may be practiced without some of these specific details. Furthermore, modifications may be made to the embodiments disclosed herein, such as, for example, to the sizes, shapes, configurations, forms, functions, materials, and manner of operation, and assembly and use, of the components of the embodiments. All equivalent relationships to those illustrated in the drawings and described in the specification are encompassed within embodiments of the invention. The scope of the invention is not to be determined by the specific examples provided above but only by the claims below. In other instances, well-known structures, devices, and operations have been shown in block diagram form or without detail in order to avoid obscuring the understanding of the description.

Elements illustrated in the figures have not necessarily been drawn to scale. For example, the dimensions of some of the elements have been exaggerated relative to others for purposes of illustration. Further, where considered appropriate, terminal portions of reference numerals have been repeated among the figures to indicate corresponding or roughly analogous elements, which may optionally have similar characteristics.

It should also be appreciated that reference throughout this specification to "one embodiment", "an embodiment", or "one or more embodiments", for example, means that a particular feature may be included in the practice of the invention. Similarly, it should be appreciated that in the description various features are sometimes grouped together in a single embodiment, Figure, or description thereof for the purpose of streamlining the disclosure and aiding in the understanding of various inventive aspects. This method of disclosure, however, is not to be interpreted as reflecting an intention that the invention requires more features than are expressly recited in each claim. Rather, as the following claims reflect, inventive aspects may lie in less than all features of a single disclosed embodiment. Thus, the claims following the Detailed Description are hereby expressly incorporated into this Detailed Description, with each claim standing on its own as a separate embodiment of the invention.

Accordingly, while the invention has been thoroughly described in terms of several embodiments, those skilled in the art will recognize that the invention is not limited to the particular embodiments described, but may be practiced with modification and alteration within the spirit and scope of the appended claims. The description is thus to be regarded as illustrative instead of limiting.

What is claimed is:

1. A scanning fiber device comprising:
    an actuator tube;
    an optical fiber inserted through the actuator tube, the optical fiber having a free end portion outside of the actuator tube;
    a first bead around the optical fiber, at least part of the first bead within a distal portion of the actuator tube;
    an adhesive adhering the first bead to the distal portion of the actuator tube;
    a second bead around the optical fiber, at least part of the second bead within a proximal portion of the actuator tube;
    an adhesive adhering the second bead to the proximal portion of the actuator tube;
    a housing enclosing the actuator tube, the free end portion, the first bead, and the second bead, in which the housing has a length that is less than 20 millimeters, and a thickness that is less than 5 millimeters; and
    one or more lenses of the housing in an optical path of light directed through the free end portion of the optical fiber.

2. The scanning fiber device of claim 1, wherein the first bead comprises a pliable material that is compressed to be within an inner diameter of the actuator tube.

3. The scanning fiber device of claim 2, wherein the second bead comprises a pliable material that is compressed to be within the inner diameter of the actuator tube.

4. The scanning fiber device of claim 3, wherein both the first and second beads are deformed to be within the inner diameter of the actuator tube.

5. The scanning fiber device of claim 3, wherein both the first and second beads have hardness less than 80 Shore A, and wherein the adhesive that adheres the first and second beads has a hardness greater than 95 Shore A.

6. The scanning fiber device of claim 1, wherein the adhesive used to adhere the first bead is different than the adhesive used to adhere the second bead.

7. The scanning fiber device of claim 6, wherein the adhesive used to adhere the second bead is harder than the adhesive used to adhere the first bead.

8. The scanning fiber device of claim 1, wherein the second bead is adhered to the actuator tube at a position where the actuator tube is coupled with the housing that encloses the actuator tube.

9. The scanning fiber device of claim 8, further comprising adhesive within the actuator tube from the proximal end of the actuator tube to just proximal to the second bead.

10. The scanning fiber device of claim 1, wherein a segment of the optical fiber between the first and second beads within the actuator tube is free of adhesive.

11. A method comprising:
applying a first bead to an optical fiber of a scanning fiber device near a proximal end of a free end portion of the optical fiber;
applying a second bead to the optical fiber at a position proximal to the first bead;
adhering at least part of the first bead within a distal portion of an actuator tube by applying and curing an adhesive; and
adhering at least part of the second bead within a proximal portion of the actuator tube by applying and curing an adhesive; and
enclosing the actuator tube, the free end portion, the first bead, and the second bead in a housing, the housing having a length that is less than 20 millimeters, and a thickness that is less than 5 millimeters.

12. The method of claim 11, further comprising introducing at least part of each of the first and second beads into the actuator tube including restraining diameters of the first and second beads to be within an inner diameter of the actuator tube.

13. The method of claim 11, wherein the first and second beads each comprises a rubbery material.

14. The method of claim 11, wherein said adhering the part of the second bead comprises adhering the part of the second bead to the actuator tube at a position where the actuator tube is coupled with the housing that encloses the actuator tube.

15. The method of claim 14, further comprising applying adhesive inside the actuator tube from just proximal to the second bead to the proximal end of the actuator tube.

16. A scanning fiber device comprising:
an actuator tube, wherein the actuator tube comprises a piezoelectric tube;
an optical fiber inserted through the actuator tube, the optical fiber having a free end portion outside of the actuator tube;
a first bead around the optical fiber, the first bead at least partially within a distal end of the actuator tube;
an adhesive adhering the first bead to the distal end of the actuator tube; and
a second bead around the optical fiber, wherein the optical fiber is attached with a proximal portion of the actuator tube with the second bead;
a housing enclosing the actuator tube, the free end portion, the first bead, and the adhesive, in which the housing has a length that is less than 20 millimeters. and a thickness that is less than 5 millimeters; and
one or more lenses of the housing in an optical path of light directed through the free end portion of the optical fiber.

17. The scanning fiber device of claim 16, wherein the first bead is more elastic than the adhesive.

18. The scanning fiber device of claim 16, wherein the first bead has a diameter that is 100% of an inner diameter of the actuator tube.

19. A method comprising:
applying a first bead to an optical fiber of a scanning fiber device near a proximal end of a free end portion of the optical fiber, wherein said applying the first bead to the optical fiber comprises applying a liquid around the optical fiber and then curing the liquid that has been applied around the optical fiber;
applying a second bead to the optical fiber;
adhering the first bead at least partially within a distal end of an actuator tube of the scanning fiber device by applying and curing an adhesive; and
attaching the optical fiber to a proximal portion of the actuator tube with the second bead.

20. The method of claim 19, wherein the first bead is more elastic than the adhesive.

21. A scanning fiber device comprising:
an actuator tube;
an optical fiber inserted through the actuator tube, the optical fiber having a free end portion outside of the actuator tube;
a first bead around the optical fiber, at least part of the first bead within a distal portion of the actuator tube, the part of the first bead within the distal portion of the actuator tube including a pliable material that is compressed to be within an inner diameter of the actuator tube;
an adhesive adhering the first bead to the distal portion of the actuator tube;
a second bead around the optical fiber, at least part of the second bead within a proximal portion of the actuator tube; and
an adhesive adhering the second bead to the proximal portion of the actuator tube.

22. The scanning fiber device of claim 21, wherein the adhesive adhering the first bead is harder than the pliable material of the first bead.

23. The scanning fiber device of claim 21, wherein the adhesive used to adhere the second bead is harder than the adhesive used to adhere the first bead.

* * * * *